US012338452B1

(12) United States Patent
Thompson

(10) Patent No.: US 12,338,452 B1
(45) Date of Patent: Jun. 24, 2025

(54) COMPOSITIONS FOR REGULATING PRODUCTION OF AN ANTIBODY LIKE PROTEIN AND RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/945,053

(22) Filed: Nov. 12, 2024

(51) Int. Cl.

| | |
|---|---|
| *C12N 15/86* | (2006.01) |
| *C07K 16/10* | (2006.01) |
| *C12N 15/113* | (2010.01) |

(52) U.S. Cl.
CPC .............. *C12N 15/86* (2013.01); *C07K 16/10* (2013.01); *C12N 15/1131* (2013.01); *C12N 2310/141* (2013.01); *C12N 2750/14143* (2013.01)

(58) Field of Classification Search
CPC ............................ C12N 15/1131; C12N 15/86
See application file for complete search history.

(56) References Cited

U.S. PATENT DOCUMENTS

| | | | | |
|---|---|---|---|---|
| 11,312,760 | B1 * | 4/2022 | Li | A61K 39/42 |
| 11,530,423 | B1 * | 12/2022 | Thompson | C12N 15/86 |
| 12,162,927 | B1 * | 12/2024 | Thompson | A61P 31/16 |

OTHER PUBLICATIONS

Lopes (Thesis: AAV-Mediated Monoclonal Antibody Expression for the Prevention of Pseudomonas Aeruginosa Infections. The University of Guelph. 2023. Published Sep. 2023) (Year: 2023).*
Bitko et al. Inhibition of respiratory viruses by nasally administered siRNA. Nature Medicine 11: 50-55. (Year: 2005).*
Skaricic et al. Genetic delivery of an anti-RSV antibody to protect against pulmonary infection with RSV. Virology 378: 79-85. (Year: 2008).*

* cited by examiner

*Primary Examiner* — James D Schultz
*Assistant Examiner* — Keenan A Bates
(74) *Attorney, Agent, or Firm* — Gowling WLG (Canada) LLP

(57) ABSTRACT

Some embodiments of the present disclosure relate to one or more compositions for regulating the production of an antibody-like protein (ALP) and ribonucleic acid (RNA). In particular, the present disclosure relates to compositions for regulating the gene expression and, therefore, the production, of an ALP and an interfering RNA (iRNA), which may suppress viral infections. In some embodiments of the present disclosure, the target viral infection is a respiratory syncytial virus (RSV) infection.

7 Claims, No Drawings

Specification includes a Sequence Listing.

COMPOSITIONS FOR REGULATING PRODUCTION OF AN ANTIBODY LIKE PROTEIN AND RIBONUCLEIC ACID

This application contains a Sequence Listing electronically submitted via Patent Center to the United States Patent and Trademark Office as an XML Document file entitled "A8149913US-SequenceListing.xml" created on 2024 Nov. 7 and having a size of 20,302 bytes. The information contained in the Sequence Listing is incorporated by reference herein.

TECHNICAL FIELD

The present disclosure generally relates to compositions for regulating the production of an antibody-like protein (ALP) and ribonucleic acid (RNA). In particular, the present disclosure relates to compositions for regulating gene expression and, therefore, the production of an ALP and interfering RNA (iRNA), which together may suppress viral infections.

BACKGROUND

Viral infections can cause mortality in subjects. In particular, viral infections may affect subjects with suppressed immune systems, for example resulting from illness or aging.

As such, it may be desirable to improve therapies and treatments for subjects with viral infections.

SUMMARY

Some embodiments of the present disclosure relate to compositions that upregulate the production of both an antibody-like protein (ALP) that targets a surface protein of a virus and one or more sequences of micro-interfering RNA (miRNA) that is complimentary to and degrades, or causes degradation of, or otherwise inactivates, the mRNA of a target, virus-specific protein or proteins.

In some embodiments of the present disclosure, the target virus is a respiratory syncytial virus (RSV). In some embodiments of the present disclosure, the target virus-specific protein is an RSV virus protein or proteins. Without being bound by any particular theory, the ALP can recognize and bind to one or more surface proteins of the target virus.

In some embodiments of the present disclosure, the composition comprises a plasmid of deoxyribonucleic acid (DNA) that includes an insert sequence of nucleotides that encode for the production of the ALP, one or more an insert sequences of nucleotides that encode for the production of miRNA and a backbone sequence of nucleotides that facilitate the introduction of the insert sequence into one or more of a subject's cells where the insert sequence is expressed and/or replicated. Expression of the insert sequence by one or more cells of the subject results in production of the ALP and production of the miRNA. The production of the ALP within one or more of the subject's cells can then bioactivate, recognize and bind to a surface protein of the infecting virus. The production of the miRNA within one or more of the subject's cells may result in decreased translation of target, virus-specific proteins by one or more of the subject's cells.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding for one or more nucleotide sequences encoding for an mRNA sequence that encodes for the ALP, and one or more nucleotide sequences encoding for miRNA against the mRNA of virus-specific proteins.

Some embodiments of the present disclosure relate to a method of making a composition/target cell complex. The method comprises a step of administering an RP comprising SEQ ID NO. 1 and SEQ ID NO. 2 to a target cell for forming the composition/target cell complex, wherein the composition/target cell complex causes the target cell to increase the production of one or more sequences of mRNA that consequently increases the production of the ALP and one or more sequences of miRNA that decreases production of virus-specific proteins.

Embodiments of the present disclosure relate to at least one approach for inducing the endogenous production of one or more sequences of mRNA that encodes for a target biomolecule, for example the ALP, and one or more sequences of miRNA that causes degradation of and/or otherwise inactivates the mRNA that encodes for virus-specific proteins.

DETAILED DESCRIPTION

Unless defined otherwise, all technical and scientific terms used therein have the meanings that would be commonly understood by one of skill in the art in the context of the present disclosure. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more immunological reactions in the subject. In some embodiments of the present disclosure, the composition is a plasmid vector.

As used therein, the term "endogenous" refers to the production and/or modification of a molecule that originates within a subject.

As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a protein molecule that is found within a subject.

As used therein, the term "target cell" refers to one or more cells and/or cell types that are affected, either directly or indirectly, by a biomolecule.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for subjects. Each unit contains a predetermined quantity of the composition and optionally, one or more suitable pharmaceutically acceptable carriers, one or more excipients, one or more additional active ingredients, or combinations thereof. The amount of the composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for the production of at least one sequence of mRNA that increases the production of target biomolecules, such as an ALP.

In some embodiments of the present disclosure, the insert comprises one or more nucleotide sequences that encode for the production of at least one sequence of miRNA that decreases the production of target biomolecules, such as virus-specific proteins.

Some embodiments of the present disclosure relate to a composition that can be administered to a subject with a condition that results, directly or indirectly, from a biomolecule. When a therapeutically effective amount of the composition is administered to the subject, the production and/or functionality of one or more of the subject's biomolecules may change as a result.

In some embodiments of the present disclosure, the production and/or functionality of one or more of a subject's intermediary molecules may change in response to the subject receiving a therapeutic amount of the composition, thereby changing production of one or more DNA sequences, one or more RNA sequences, and/or one or more proteins that regulate the levels and/or functionality of the one or more intermediary molecules. The one or more intermediary molecules may regulate the subject's levels and/or functionality of the one or more biomolecules.

In some embodiments of the present disclosure, administering a therapeutic amount of the composition to a subject upregulates the production, functionality or both of one or more sequences of mRNA that each encode for one or more biomolecules.

In some embodiments of the present disclosure, the composition is an RP that may be used for gene therapy.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a subject is between about 10 and about $1\times10^{16}$ $TCID_{50}$/kg (50% tissue culture infective dose per kilogram of the subject's body mass). In some embodiments of the present disclosure, the therapeutically effective amount of the composition that is administered to the subject is about $1\times10^{13}$ $TCID_{50}$/kg. In some embodiments of the present disclosure, the therapeutically effective amount of the composition that is administered to a subject is measured in TPC/kg (total particle count of the composition per kilogram of the subject's body mass). In some embodiments of the present disclosure, the therapeutically effective amount of the composition is between about 10 and about $1\times10^{16}$ TCP/kg.

Some embodiments of the present disclosure relate to an adeno-associated virus (AAV) genome consisting of an RP that, when operable inside a target cell, will cause the target cell to produce an mRNA sequence that upregulates the production of a biomolecule, with an example being an ALP, and miRNA sequences that down regulate the production of a biomolecule, with an example being a virus-specific protein. The RP is comprised of AAV2 inverted terminal repeats (ITRs), a composite CASI promoter, and a human growth hormone (HGH) signal peptide, followed by an expression cassette, followed by a Woodchuck Hepatitis Virus post-transcriptional regulatory element (WPRE) and a Simian virus 40 (SV40) polyadenylation (polyA) signal.

```
SEQ ID NO. 1 (backbone sequence No. 1):
5'

TCTAGAAAGCTTCGATAATCAACCTCTGGATTACAAAATTTGTGAAAGATTGACTGG

TATTCTTAACTATGTTGCTCCTTTTACGCTATGTGGATACGCTGCTTTAATGCCTTTGT

ATCATGCTATTGCTTCCCGTATGGCTTTCATTTTCTCCTCCTTGTATAAATCCTGGTTG

CTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTT

TCCGGGACTTTCGCTTTCCCCCTCCCTATTGCCACGGCGGAACTCATCGCCGCCTGCC

TTGCCCGCTGCTGGACAGGGGCTCGGCTGTTGGGCACTGACAATTCCGTGGTGTTGT

CGGGGAAATCATCGTCCTTTCCTTGGCTGCTCGCCTGTGTTGCCACCTGGATTCTGCG

CGGGACGTCCTTCTGCTACGTCCCTTCGGCCCTCAATCCAGCGGACCTTCCTTCCCGC

GGCCTGCTGCCGGCTCTGCGGCCTCTTCCGCGTCTTCGCCTTCGCCCTCAGACGAGTC

GGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACA

AATAAAGCATTTTTTTCACTGCATTCTAGTTGTGGTTTGTCCAAACTCATCAATGTAT

CTTATCATGTCTGGATCTCGACCTCGACTAGAGCATGGCTACGTAGATAAGTAGCAT

GGCGGGTTAATCATTAACTACAAGGAACCCCTAGTGATGGAGTTGGCCACTCCCTCT

CTGCGCGCTCGCTCGCTCACTGAGGCCGGGCGACCAAAGGTCGCCCGACGCCCGGG

CTTTGCCCGGGCGGCCTCAGTGAGCGAGCGAGCGCGCAGCTGGCGTAATAGCGAAG

AGGCCCGCACCGATCGCCCTTCCCAACAGTTGCGCAGCCTGAATGGCGAATGGCGA

TTCCGTTGCAATGGCTGGCGGTAATATTGTTCTGGATATTACCAGCAAGGCCGATAG

TTTGAGTTCTTCTACTCAGGCAAGTGATGTTATTACTAATCAAAGAAGTATTGCGAC

AACGGTTAATTTGCGTGATGGACAGACTCTTTTACTCGGTGGCCTCACTGATTATAA

AAACACTTCTCAGGATTCTGGCGTACCGTTCCTGTCTAAAATCCCTTTAATCGGCCTC

CTGTTTAGCTCCCGCTCTGATTCTAACGAGGAAAGCACGTTATACGTGCTCGTCAAA

GCAACCATAGTACGCGCCCTGTAGCGGCGCATTAAGCGCGGCGGGTGTGGTGGTTA

CGCGCAGCGTGACCGCTACACTTGCCAGCGCCCTAGCGCCCGCTCCTTTCGCTTTCTT

CCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACG
```

-continued

```
TTGGAGTCCACGTTCTTTAATAGTGGACTCTTGTTCCAAACTGGAACAACACTCAAC

CCTATCTCGGTCTATTCTTTTGATTTATAAGGGATTTTGCCGATTTCGGCCTATTGGTT

AAAAAATGAGCTGATTTAACAAAAATTTAACGCGAATTTTAACAAAATATTAACGTT

TACAATTTAAATATTTGCTTATACAATCTTCCTGTTTTTGGGCTTTTCTGATTATCAA

CCGGGGTACATATGATTGACATGCTAGTTTTACGATTACCGTTCATCGATTCTCTTGT

TTGCTCCAGACTCTCAGGCAATGACCTGATAGCCTTTGTAGAGACCTCTCAAAAATA

GCTACCCTCTCCGGCATGAATTTATCAGCTAGAACGGTTGAATATCATATTGATGGT

GATTTGACTGTCTCCGGCCTTTCTCACCCGTTTGAATCTTTACCTACACATTACTCAG

GCATTGCATTTAAAATATATGAGGGTTCTAAAAATTTTTATCCTTGCGTTGAAATAA

AGGCTTCTCCCGCAAAAGTATTACAGGGTCATAATGTTTTTGGTACAACCGATTTAG

CTTTATGCTCTGAGGCTTTATTGCTTAATTTTGCTAATTCTTTGCCTTGCCTGTATGAT

TTATTGGATGTTGGAATTCCTGATGCGGTATTTTCTCCTTACGCATCTGTGCGGTATT

TCACACCGCATATGGTGCACTCTCAGTACAATCTGCTCTGATGCCGCATAGTTAAGC

CAGCCCCGACACCCGCCAACACCCGCTGACGCGCCCTGACGGGCTTGTCTGCTCCCG

GCATCCGCTTACAGACAAGCTGTGACCGTCTCCGGGAGCTGCATGTGTCAGAGGTTT

TCACCGTCATCACCGAAACGCGCGAGACGAAAGGGCCTCGTGATACGCCTATTTTTA

TAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGC

TCATGAGACAATAACCCTGATAAATGCTTCAATAATATTGAAAAAGGAAGAGTATG

AGTATTCAACATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGTTGGGTG

CACGAGTGGGTTACATCGAACTGGATCTCAACAGCGGTAAGATCCTTGAGAGTTTTC

GCCCCGAAGAACGTTTTCCAATGATGAGCACTTTTAAAGTTCTGCTATGTGGCGCGG

TATTATCCCGTATTGACGCCGGGCAAGAGCAACTCGGTCGCCGCATACACTATTCTC

AGAATGACTTGGTTGAGTACTCACCAGTCACAGAAAAGCATCTTACGGATGGCATG

ACAGTAAGAGAATTATGCAGTGCTGCCATAACCATGAGTGATAACACTGCGGCCAA

CTTACTTCTGACAACGATCGGAGGACCGAAGGAGCTAACCGCTTTTTTGCACAACAT

GGGGGATCATGTAACTCGCCTTGATCGTTGGGAACCGGAGCTGAATGAAGCCATAC

CAAACGACGAGCGTGACACCACGATGCCTGTAGCAATGGCAACAACGTTGCGCAAA

CTATTAACTGGCGAACTACTTACTCTAGCTTCCCGGCAACAATTAATAGACTGGATG

GAGGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGC

AACTATGGATGAACGAAATAGACAGATCGCTGAGATAGGTGCCTCACTGATTAAGC

ATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATC

CCTTAACGTGAGTTTTCGTTCCACTGAGCGTCAGACCCCGTAGAAAAGATCAAAGGA

TCTTCTTGAGATCCTTTTTTTCTGCGCGTAATCTGCTGCTTGCAAACAAAAAAACCAC

CGCTACCAGCGGTGGTTTGTTTGCCGGATCAAGAGCTACCAACTCTTTTTCCGAAGG

TAACTGGCTTCAGCAGAGCGCAGATACCAAATACTGTCCTTCTAGTGTAGCCGTAGT
```

-continued

```
TAGGCCACCACTTCAAGAACTCTGTAGCACCGCCTACATACCTCGCTCTGCTAATCC

TGTTACCAGTGGCTGCTGCCAGTGGCGATAAGTCGTGTCTTACCGGGTTGGACTCAA

GACGATAGTTACCGGATAAGGCGCAGCGGTCGGGCTGAACGGGGGGTTCGTGCACA

CAGCCCAGCTTGGAGCGAACGACCTACACCGAACTGAGATACCTACAGCGTGAGCT

ATGAGAAAGCGCCACGCTTCCCGAAGGGAGAAAGGCGGACAGGTATCCGGTAAGC

GGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATG

CTCGTCAGGGGGCGGAGCCTATGGAAAAACGCCAGCAACGCGGCCTTTTTACGGT

TCCTGGCCTTTTGCTGGCCTTTTGCTCACATGTTCTTTCCTGCGTTATCCCCTGATTCT

GTGGATAACCGTATTACCGCCTTTGAGTGAGCTGATACCGCTCGCCGCAGCCGAACG

ACCGAGCGCAGCGAGTCAGTGAGCGAGGAAGCGGAAGAGCGCCCAATACGCAAAC

CGCCTCTCCCCGCGCGTTGGCCGATTCATTAATGCAGCAGCTGCGCGCTCGCTCGCT

CACTGAGGCCGCCCGGGCAAAGCCCGGGCGTCGGGCGACCTTTGGTCGCCCGGCCT

CAGTGAGCGAGCGAGCGCGCAGAGAGGGAGTGGCCAACTCCATCACTAGGGGTTCC

TTGTAGTTAATGATTAACCCGCCATGCTACTTATCTACGTAGCCATGCTCTAGGACAT

TGATTATTGACTAGTGGAGTTCCGCGTTACATAACTTACGGTAAATGGCCCGCCTGG

CTGACCGCCCAACGACCCCCGCCCATTGACGTCAATAATGACGTATGTTCCCATAGT

AACGCCAATAGGGACTTTCCATTGACGTCAATGGGTGGAGTATTTACGGTAAACTGC

CCACTTGGCAGTACATCAAGTGTATCATATGCCAAGTACGCCCCCTATTGACGTCAA

TGACGGTAAATGGCCCGCCTGGCATTATGCCCAGTACATGACCTTATGGGACTTTCC

TACTTGGCAGTACATCTACGTATTAGTCATCGCTATTACCATGGTCGAGGTGAGCCC

CACGTTCTGCTTCACTCTCCCCATCTCCCCCCCCTCCCCACCCCCAATTTTGTATTTAT

TTATTTTTTAATTATTTTGTGCAGCGATGGGGGCGGGGGGGGGGGGGCGCGCGCC

AGGCGGGCGGGGCGGGGCGAGGGGCGGGGCGGGGCGAGGCGGAGAGGTGCGGC

GGCAGCCAATCAGAGCGGCGCGCTCCGAAAGTTTCCTTTTATGGCGAGGCGGCGGC

GGCGGCGGCCCTATAAAAAGCGAAGCGCGCGGCGGGCGGGAGTCGCTGCGCGCTGC

CTTCGCCCCGTGCCCCGCTCCGCCGCCGCCTCGCGCCGCCCGCCCCGGCTCTGACTG

ACCGCGTTACTAAAACAGGTAAGTCCGGCCTCCGCGCCGGGTTTTGGCGCCTCCCGC

GGGCGCCCCCCTCCTCACGGCGAGCGCTGCCACGTCAGACGAAGGGCGCAGCGAGC

GTCCTGATCCTTCCGCCCGGACGCTCAGGACAGCGGCCCGCTGCTCATAAGACTCGG

CCTTAGAACCCCAGTATCAGCAGAAGGACATTTTAGGACGGGACTTGGGTGACTCTA

GGGCACTGGTTTTCTTTCCAGAGAGCGGAACAGGCGAGGAAAAGTAGTCCCTTCTCG

GCGATTCTGCGGAGGGATCTCCGTGGGGCGGTGAACGCCGATGATGCCTCTACTAAC

CATGTTCATGTTTTCTTTTTTTTCTACAGGTCCTGGGTGACGAACAGGGTACC

3'

SEQ ID NO. 2 (mRNA and miRNA expression cassette No. 2):
5'

GCCACCATGGCTACTGGGTCAAGAACATCTCTGCTGCTGGCTTTCGGGCTGCTGTGC

CTGCCTTGGCTGCAGGAGGGGAGTGCTCAGGTCCAGCTGGTGGAGTCTGGTCCTGCG

CTGGTGAAACCCACACAGACCCTCACACTGACCTGCAGCTTCTCCGGGTTCTCACTC

ACCACTAGGAGAATGTGTGTGAGCTGGATCCGTCAGACCCCAGGGAAGGCCCTGGA
```

-continued

```
GTGGCTTGCACGCATTGATTGGGATGATGATAAAGACTACAGCACATCTCTGAAGAC
CAGGCTCACCATCTCCAAGGACACCTCCAAAAACCAGGTGGTCCTTACAATGACCA
ACATGGACCCTGTGGACACGGCCACGTATTACTGTGCCACGGACCCACATTTATGAT
AGTAGTGGTTATTATCTATACTACTTTGACTACTGGGGCCAGGGAACCCTGGTCACG
TCTCTTCATCCACAAAGGGCCCAAGCGTGTTTCCTCTGGCCCCATCTAGCAAGAGCA
CATCCGGAGGCACCGCCGCCCTGGGATGTCTGGTGAAGGATTACTTCCCAGAGCCC
GTGACCGTGTCTTGGAACAGCGGCGCCCTGACATCCGGAGTGCACACCTTTCCAGCC
GTGCTGCAGTCCTCTGGCCTGTACAGCCTGAGCTCCGTGGTGACAGTGCCTTCTAGC
TCCCTGGGCACACAGACCTATATCTGCAACGTGAATCACAAGCCCAGCAATACCAA
GGTGGACAAGAAGGTGGAGCCTAAGTCCTGTGATAAGACACACACCTGCCCACCAT
GTCCTGCACCAGAGCTGCTGGGAGGACCATCCGTGTTCCTGTTTCCTCCAAAGCCCA
AGGACACACTGATGATCTCTCGCACACCCGAGGTGACCTGCGTGGTGGTGGACGTG
AGCCACGAGGATCCTGAGGTGAAGTTCAACTGGTACGTGGATGGCGTGGAGGTGCA
CAATGCCAAGACCAAGCCTAGAGAGGAGCAGTACAACAGCACATATCGGGTGGTGT
CCGTGCTGACCGTGCTGCACCAGGACTGGCTGAACGGCAAGGAGTATAAGTGCAAG
GTGTCCAATAAGGCCCTGCCCGCCCCTATCGAGAAGACAATCTCTAAGGCAAAGGG
ACAGCCAAGGGAGCCTCAGGTGTACACCCTGCCCCCTTCCAGGGAGGAGATGACAA
AGAACCAGGTGTCTCTGACCTGTCTGGTGAAGGGCTTCTATCCTTCCGACATCGCCG
TGGAGTGGGAGTCTAATGGCCAGCCAGAGAACAATTACAAGACCACACCACCCGTG
CTGGACTCCGATGGCTCTTTCTTTCTGTATTCTAAGCTGACCGTGGATAAGAGCAGA
TGGCAGCAGGGCAACGTGTTTTCTTGTAGCGTGATGCACGAGGCCCTGCACAATCAC
TACACACAGAAGTCCCTGTCTCTGAGCCCAGGCAAGAGGAAGAGGAGATCCGGATC
TGGAGCACCAGTGAAGCAGACCCTGAACTTCGACCTGCTGAAGCTGGCCGGCGATG
TGGAGAGCAATCCAGGCCCCATGGCCACAGGCAGCAGAACCTCCCTGCTGCTGGCC
TTTGGCCTGCTGTGCCTGCCATGGCTGCAGGAGGGAAGCGCCGATATTGTGCTGACC
CAGTCTCCATCCTCCCTGTCTGCATCTATAGGAGACAGAGTCACCATCACTTGCCGG
GCAAGTCAGACCATTGCCAGCTATTTAAATGGTATCAGCAGAAACCAGGGAAAGCC
CCTGAACTCCTGATCTATGCTGCAACCAATTTGCAGAGTGGGGTCCCATCAAGGTTC
AGTGGCAGTGGATCTGGGACAGATTTCACTCTCACCATCAGCAGTCTGCGACCTGAA
GATTTTGCAAGTTACTACTGTCAACAGAGTTACAGTAGTCCCTGGACGTTCGGCCAA
GGGACCAAAGTGGATATCAAAAGGACAGCCTAAGGCAGCACCATCCGTGACCCTGT
TCCCACCTTCCTCTGAGGAGCTGCAGGCCAATAAGGCCACCCTGGTGTGCCTGATCA
GCGACTTTTACCCTGGAGCAGTGACCGTGGCATGGAAGGCCGATAGCTCCCCTGTGA
AGGCCGGCGTGGAGACAACAACCCCATCTAAGCAGAGCAACAATAAGTACGCCGCC
TCTAGCTATCTGTCTCTGACCCCAGAGCAGTGGAAGAGCCACCGGTCTTATAGCTGT
CAGGTGACCCATGAAGGCTCAACTGTGGAGAAAACCGTCGCCCCAACTGAATGTTC
CTAACGAGCTCGGTACCTCTAGATGCTGGAGGCTTGCTGAAGGCTGTATGCTGGCCA
GGAACTGAAATTGATACCAGTTTTGGCCTCTGACTGACTGGTATCAATCAGTTCCTG
GCCAGGACACAAGGCCTGTTACTAGCACTCACATGGAACAAATGGCCTCTAGCCTG
GAGGCTTGCTGAAGGCTGTATGCTGGCCTGCGCGTGTGATGATTAACAGTTTTGGCC
TCTGACTGACTGTTAATCATCACGCGCAGGCCAGGACACAAGGCCTGTTACTAGCAC
```

-continued

TCACATGGAACAAATGGCCTCTAGCCTGGAGGCTTGCTGAAGGCTGTATGCTGGCAA

ACTGCTGATACCGAACTGAGTTTTGGCCTCTGACTGACTCAGTTCGGTCAGCAGTTT

GCCAGGACACAAGGCCTGTTACTAGCACTCACATGGAACAAATGGCCTC

3'

SEQ ID NO. 3 = SEQ ID NO. 1 + SEQ ID NO. 2
5'

TCTAGAAAGCTTCGATAATCAACCTCTGGATTACAAAATTTGTGAAAGATTGACTGG

TATTCTTAACTATGTTGCTCCTTTTACGCTATGTGGATACGCTGCTTTAATGCCTTTGT

ATCATGCTATTGCTTCCCGTATGGCTTTCATTTTCTCCTCCTTGTATAAATCCTGGTTG

CTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTT

TCCGGGACTTTCGCTTTCCCCCTCCCTATTGCCACGGCGGAACTCATCGCCGCCTGCC

TTGCCCGCTGCTGGACAGGGGCTCGGCTGTTGGGCACTGACAATTCCGTGGTGTTGT

CGGGGAAATCATCGTCCTTTCCTTGGCTGCTCGCCTGTGTTGCCACCTGGATTCTGCG

CGGGACGTCCTTCTGCTACGTCCCTTCGGCCCTCAATCCAGCGGACCTTCCTTCCCGC

GGCCTGCTGCCGGCTCTGCGGCCTCTTCCGCGTCTTCGCCTTCGCCCTCAGACGAGTC

GGATCTCCCTTTGGGCCGCCTCCCCGCCTAAGCTTATCGATACCGTCGAGATCTAAC

TTGTTTATTGCAGCTTATAATGGTTACAAATAAAGCAATAGCATCACAAATTTCACA

AATAAAGCATTTTTTTCACTGCATTCTAGTTGTGGTTTGTCCAAACTCATCAATGTAT

CTTATCATGTCTGGATCTCGACCTCGACTAGAGCATGGCTACGTAGATAAGTAGCAT

GGCGGGTTAATCATTAACTACAAGGAACCCCTAGTGATGGAGTTGGCCACTCCCTCT

CTGCGCGCTCGCTCGCTCACTGAGGCCGGGCGACCAAAGGTCGCCCGACGCCCGGG

CTTTGCCCGGGCGGCCTCAGTGAGCGAGCGAGCGCGCAGCTGGCGTAATAGCGAAG

AGGCCCGCACCGATCGCCCTTCCCAACAGTTGCGCAGCCTGAATGGCGAATGGCGA

TTCCGTTGCAATGGCTGGCGGTAATATTGTTCTGGATATTACCAGCAAGGCCGATAG

TTTGAGTTCTTCTACTCAGGCAAGTGATGTTATTACTAATCAAAGAAGTATTGCGAC

AACGGTTAATTTGCGTGATGGACAGACTCTTTTACTCGGTGGCCTCACTGATTATAA

AAACACTTCTCAGGATTCTGGCGTACCGTTCCTGTCTAAAATCCCTTTAATCGGCCTC

CTGTTTAGCTCCCGCTCTGATTCTAACGAGGAAAGCACGTTATACGTGCTCGTCAAA

GCAACCATAGTACGCGCCCTGTAGCGGCGCATTAAGCGCGGCGGGTGTGGTGGTTA

CGCGCAGCGTGACCGCTACACTTGCCAGCGCCCTAGCGCCCGCTCCTTTCGCTTTCTT

CCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACG

TTGGAGTCCACGTTCTTTAATAGTGGACTCTTGTTCCAAACTGGAACAACACTCAAC

CCTATCTCGGTCTATTCTTTTGATTTATAAGGGATTTTGCCGATTTCGGCCTATTGGTT

AAAAAATGAGCTGATTTAACAAAAATTTAACGCGAATTTTAACAAAATATTAACGTT

TACAATTTAAATATTTGCTTATACAATCTTCCTGTTTTTGGGGCTTTTCTGATTATCAA

CCGGGGTACATATGATTGACATGCTAGTTTTACGATTACCGTTCATCGATTCTCTTGT

TTGCTCCAGACTCTCAGGCAATGACCTGATAGCCTTTGTAGAGACCTCTCAAAAATA

GCTACCCTCTCCGGCATGAATTTATCAGCTAGAACGGTTGAATATCATATTGATGGT

-continued

```
GATTTGACTGTCTCCGGCCTTTCTCACCCGTTTGAATCTTTACCTACACATTACTCAG

GCATTGCATTTAAAATATATGAGGGTTCTAAAAATTTTTATCCTTGCGTTGAAATAA

AGGCTTCTCCCGCAAAAGTATTACAGGGTCATAATGTTTTTGGTACAACCGATTTAG

CTTTATGCTCTGAGGCTTTATTGCTTAATTTTGCTAATTCTTTGCCTTGCCTGTATGAT

TTATTGGATGTTGGAATTCCTGATGCGGTATTTTCTCCTTACGCATCTGTGCGGTATT

TCACACCGCATATGGTGCACTCTCAGTACAATCTGCTCTGATGCCGCATAGTTAAGC

CAGCCCCGACACCCGCCAACACCCGCTGACGCGCCCTGACGGGCTTGTCTGCTCCCG

GCATCCGCTTACAGACAAGCTGTGACCGTCTCCGGGAGCTGCATGTGTCAGAGGTTT

TCACCGTCATCACCGAAACGCGCGAGACGAAAGGGCCTCGTGATACGCCTATTTTTA

TAGGTTAATGTCATGATAATAATGGTTTCTTAGACGTCAGGTGGCACTTTTCGGGGA

AATGTGCGCGGAACCCCTATTTGTTTATTTTTCTAAATACATTCAAATATGTATCCGC

TCATGAGACAATAACCCTGATAAATGCTTCAATAATATTGAAAAAGGAAGAGTATG

AGTATTCAACATTTCCGTGTCGCCCTTATTCCCTTTTTTGCGGCATTTTGCCTTCCTGT

TTTTGCTCACCCAGAAACGCTGGTGAAAGTAAAAGATGCTGAAGATCAGTTGGGTG

CACGAGTGGGTTACATCGAACTGGATCTCAACAGCGGTAAGATCCTTGAGAGTTTTC

GCCCCGAAGAACGTTTTCCAATGATGAGCACTTTTAAAGTTCTGCTATGTGGCGCGG

TATTATCCCGTATTGACGCCGGGCAAGAGCAACTCGGTCGCCGCATACACTATTCTC

AGAATGACTTGGTTGAGTACTCACCAGTCACAGAAAAGCATCTTACGGATGGCATG

ACAGTAAGAGAATTATGCAGTGCTGCCATAACCATGAGTGATAACACTGCGGCCAA

CTTACTTCTGACAACGATCGGAGGACCGAAGGAGCTAACCGCTTTTTTGCACAACAT

GGGGGATCATGTAACTCGCCTTGATCGTTGGGAACCGGAGCTGAATGAAGCCATAC

CAAACGACGAGCGTGACACCACGATGCCTGTAGCAATGGCAACAACGTTGCGCAAA

CTATTAACTGGCGAACTACTTACTCTAGCTTCCCGGCAACAATTAATAGACTGGATG

GAGGCGGATAAAGTTGCAGGACCACTTCTGCGCTCGGCCCTTCCGGCTGGCTGGTTT

ATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGC

AACTATGGATGAACGAAATAGACAGATCGCTGAGATAGGTGCCTCACTGATTAAGC

ATTGGTAACTGTCAGACCAAGTTTACTCATATATACTTTAGATTGATTTAAAACTTCA

TTTTTAATTTAAAAGGATCTAGGTGAAGATCCTTTTTGATAATCTCATGACCAAAATC

CCTTAACGTGAGTTTTCGTTCCACTGAGCGTCAGACCCCGTAGAAAAGATCAAAGGA

TCTTCTTGAGATCCTTTTTTTCTGCGCGTAATCTGCTGCTTGCAAACAAAAAAACCAC

CGCTACCAGCGGTGGTTTGTTTGCCGGATCAAGAGCTACCAACTCTTTTTCCGAAGG

TAACTGGCTTCAGCAGAGCGCAGATACCAAATACTGTCCTTCTAGTGTAGCCGTAGT

TAGGCCACCACTTCAAGAACTCTGTAGCACCGCCTACATACCTCGCTCTGCTAATCC

TGTTACCAGTGGCTGCTGCCAGTGGCGATAAGTCGTGTCTTACCGGGTTGGACTCAA

GACGATAGTTACCGGATAAGGCGCAGCGGTCGGGCTGAACGGGGGGTTCGTGCACA

CAGCCCAGCTTGGAGCGAACGACCTACACCGAACTGAGATACCTACAGCGTGAGCT

ATGAGAAAGCGCCACGCTTCCCGAAGGGAGAAAGGCGGACAGGTATCCGGTAAGC

GGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATG
```

-continued

```
CTCGTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCTGATTCT
GTGGATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCCAATACGCAAAC
CGCCTCTCCCCGCGCGTTGGCCGATTCATTAATGCAGCAGCTGCGCGCTCGCTCGCT
CACTGAGGCCGCCCGGGCAAAGCCCGGGCGTCGGGCGACCTTTGGTCGCCCGGCCT
CAGTGAGCGAGCGAGCGCGCAGAGAGGGAGTGGCCAACTCCATCACTAGGGGTTCC
TTGTAGTTAATGATTAACCCGCCATGCTACTTATCTACGTAGCCATGCTCTAGGACAT
TGATTATTGACTAGTGGAGTTCCGCGTTACATAACTTACGGTAAATGGCCCGCCTGG
CTGACCGCCCAACGACCCCCGCCCATTGACGTCAATAATGACGTATGTTCCCATAGT
AACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAA
TGACGGTAAATGGCCCGCCTGGCATTATGCCCAGTACATGACCTTATGGGACTTTCC
TACTTGGCAGTACATCTACGTATTAGTCATCGCTATTACCATGGTCGAGGTGAGCCC
CACGTTCTGCTTCACTCTCCCCATCTCCCCCCCCTCCCCACCCCCAATTTTGTATTTAT
TTATTTTTTAATTATTTTGTGCAGCGATGGGGGCGGGGGGGGGGGGGCGCGCGCC
AGGCGGGGGGGCGGGGCGAGGGGCGGGGCGGGGCGAGGCGGAGAGGTGCGGC
GGCAGCCAATCAGAGCGGCGCGCTCCGAAAGTTTCCTTTTATGGCGAGGCGGCGGC
GGCGGCGGCCCTATAAAAAGCGAAGCGCGCGGCGGGGGGAGTCGCTGCGCGCTGC
CTTCGCCCCGTGCCCCGCTCCGCCGCCGCCTCGCGCCGCCCGCCCCGGCTCTGACTG
ACCGCGTTACTAAAACAGGTAAGTCCGGCCTCCGCGCCGGGTTTTGGCGCCTCCCGC
GGGCGCCCCCCTCCTCACGGCGAGCGCTGCCACGTCAGACGAAGGGCGCAGCGAGC
GTCCTGATCCTTCCGCCCGGACGCTCAGGACAGCGGCCCGCTGCTCATAAGACTCGG
CCTTAGAACCCCAGTATCAGCAGAAGGACATTTTAGGACGGGACTTGGGTGACTCTA
GGGCACTGGTTTTCTTTCCAGAGAGCGGAACAGGCGAGGAAAAGTAGTCCCTTCTCG
GCGATTCTGCGGAGGGATCTCCGTGGGCGGTGAACGCCGATGATGCCTCTACTAAC
CATGTTCATGTTTTCTTTTTTTTTCTACAGGTCCTGGGTGACGAACAGGGTACCGCCA
CCATGGCTACTGGGTCAAGAACATCTCTGCTGCTGGCTTTCGGGCTGCTGTGCCTGC
CTTGGCTGCAGGAGGGGAGTGCTCAGGTCCAGCTGGTGGAGTCTGGTCCTGCGCTGG
TGAAACCCACACAGACCCTCACACTGACCTGCAGCTTCTCCGGGTTCTCACTCACCA
CTAGGAGAATGTGTGTGAGCTGGATCCGTCAGACCCCAGGGAAGGCCCTGGAGTGG
CTTGCACGCATTGATTGGGATGATGATAAAGACTACAGCACATCTCTGAAGACCAG
GCTCACCATCTCCAAGGACACCTCCAAAAACCAGGTGGTCCTTACAATGACCAACAT
GGACCCTGTGGACACGGCCACGTATTACTGTGCCACGGACCCACATTTATGATAGTA
GTGGTTATTATCTATACTACTTTGACTACTGGGGCCAGGGAACCCTGGTCACGTCTCT
TCATCCACAAAGGGCCCAAGCGTGTTTCCTCTGGCCCCATCTAGCAAGAGCACATCC
GGAGGCACCGCCGCGCCCTGGGATGTCTGGTGAAGGATTACTTCCCAGAGCCCGTGAC
CGTGTCTTGGAACAGCGGCGCCCTGACATCCGGAGTGCACACCTTTCCAGCCGTGCT
GCAGTCCTCTGGCCTGTACAGCCTGAGCTCCGTGGTGACAGTGCCTTCTAGCTCCCT
GGGCACACAGACCTATATCTGCAACGTGAATCACAAGCCCAGCAATACCAAGGTGG
ACAAGAAGGTGGAGCCTAAGTCCTGTGATAAGACACACACCTGCCCACCATGTCCT
```

-continued

```
GCACCAGAGCTGCTGGGAGGACCATCCGTGTTCCTGTTTCCTCCAAAGCCCAAGGAC
ACACTGATGATCTCTCGCACACCCGAGGTGACCTGCGTGGTGGTGGACGTGAGCCA
CGAGGATCCTGAGGTGAAGTTCAACTGGTACGTGGATGGCGTGGAGGTGCACAATG
CCAAGACCAAGCCTAGAGAGGAGCAGTACAACAGCACATATCGGGTGGTGTCCGTG
CTGACCGTGCTGCACCAGGACTGGCTGAACGGCAAGGAGTATAAGTGCAAGGTGTC
CAATAAGGCCCTGCCCGCCCCTATCGAGAAGACAATCTCTAAGGCAAAGGGACAGC
CAAGGGAGCCTCAGGTGTACACCCTGCCCCCTTCCAGGGAGGAGATGACAAAGAAC
CAGGTGTCTCTGACCTGTCTGGTGAAGGGCTTCTATCCTTCCGACATCGCCGTGGAG
TGGGAGTCTAATGGCCAGCCAGAGAACAATTACAAGACCACACCACCCGTGCTGGA
CTCCGATGGCTCTTTCTTTCTGTATTCTAAGCTGACCGTGGATAAGAGCAGATGGCA
GCAGGGCAACGTGTTTTCTTGTAGCGTGATGCACGAGGCCCTGCACAATCACTACAC
ACAGAAGTCCCTGTCTCTGAGCCCAGGCAAGAGGAAGAGGAGATCCGGATCTGGAG
CACCAGTGAAGCAGACCCTGAACTTCGACCTGCTGAAGCTGGCCGGCGATGTGGAG
AGCAATCCAGGCCCCATGGCCACAGGCAGCAGAACCTCCCTGCTGCTGGCCTTTGGC
CTGCTGTGCCTGCCATGGCTGCAGGAGGGAAGCGCCGATATTGTGCTGACCCAGTCT
CCATCCTCCCTGTCTGCATCTATAGGAGACAGAGTCACCATCACTTGCCGGGCAAGT
CAGACCATTGCCAGCTATTTAAATGGTATCAGCAGAAACCAGGGAAAGCCCCTGAA
CTCCTGATCTATGCTGCAACCAATTTGCAGAGTGGGGTCCCATCAAGGTTCAGTGGC
AGTGGATCTGGGACAGATTTCACTCTCACCATCAGCAGTCTGCGACCTGAAGATTTT
GCAAGTTACTACTGTCAACAGAGTTACAGTAGTCCCTGGACGTTCGGCCAAGGGACC
AAAGTGGATATCAAAAGGACAGCCTAAGGCAGCACCATCCGTGACCCTGTTCCCAC
CTTCCTCTGAGGAGCTGCAGGCCAATAAGGCCACCCTGGTGTGCCTGATCAGCGACT
TTTACCCTGGAGCAGTGACCGTGGCATGGAAGGCCGATAGCTCCCCTGTGAAGGCC
GGCGTGGAGACAACAACCCCATCTAAGCAGAGCAACAATAAGTACGCCGCCTCTAG
CTATCTGTCTCTGACCCCAGAGCAGTGGAAGAGCCACCGGTCTTATAGCTGTCAGGT
GACCCATGAAGGCTCAACTGTGGAGAAAACCGTCGCCCCAACTGAATGTTCCTAAC
GAGCTCGGTACCTCTAGATGCTGGAGGCTTGCTGAAGGCTGTATGCTGGCCAGGAAC
TGAAATTGATACCAGTTTTGGCCTCTGACTGACTGGTATCAATCAGTTCCTGGCCAG
GACACAAGGCCTGTTACTAGCACTCACATGGAACAAATGGCCTCTAGCCTGGAGGC
TTGCTGAAGGCTGTATGCTGGCCTGCGCGTGTGATGATTAACAGTTTTGGCCTCTGA
CTGACTGTTAATCATCACGCGCAGGCCAGGACACAAGGCCTGTTACTAGCACTCACA
TGGAACAAATGGCCTCTAGCCTGGAGGCTTGCTGAAGGCTGTATGCTGGCAAACTGC
TGATACCGAACTGAGTTTTGGCCTCTGACTGACTCAGTTCGGTCAGCAGTTTGCCAG
GACACAAGGCCTGTTACTAGCACTCACATGGAACAAATGGCCTC
```
3'

As will be appreciated by those skilled in the art, because the recombinant plasmid is a circular vector, the one or more sequences of the mRNA expression cassettes may be connected at the 3' end of SEQ ID NO. 1, as shown in SEQ ID NO. 3, or at the 5' end of SEQ ID NO. 1.

As will be appreciated by those skilled in the art, a perfect match of nucleotides with each of the expression cassette sequences is not necessary in order to have the desired result of increased bioavailability of the ALP as a result of the target cell producing the mRNA sequence that code for the expression of the ALP, and decreased bioavailability of the virus-specific proteins as a result of the target cell producing the miRNA sequences that target the mRNA encoding for the virus-specific proteins. In some embodiments of the present disclosure, about 80% to about 100% nucleotide sequence matching, or about 80% to about 100% identical nucleotide sequences, with each of the expression cassettes causes the desired result. In some embodiments of the present disclosure, about 85% to about 100% nucleotide sequence matching with each of the expression cassettes causes the desired result. In some embodiments of the present disclosure, about 90% to about 100% nucleotide sequence matching with each of the expression cassettes causes the desired result. In some embodiments of the present disclosure, about 95% to about 100% nucleotide sequence matching with each of the expression cassettes causes the desired result.

Example 1—Expression Cassette

Expression cassettes for expressing mRNA were synthesized. The synthesized mRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each expression cassette was amplified by polymerase chain reaction (PCR) using Taq polymerase and the PCR products were gel purified and the bands on interest were also excised and purified using a gel extraction kit. These PCR products contained the expression cassettes in addition to 15 base pair 5' and 3' overhangs that aligned with the ends of the linearized pAVA-00200 backbone. Using in-fusion cloning, the amplified expression cassettes were integrated with the pAVA-00200 backbone via homologous recombination. The resulting RP contained the following: 5' ITR, CASI promoter, expression cassette, WPRE, SV40 polyA and ITR 3'.

The invention claimed is:

1. A composition that comprises a recombinant plasmid (RP) with a sequence of nucleotides that is SEQ ID NO. 2.

2. The composition of claim 1, wherein the RP is configured to be delivered to a target cell.

3. The composition of claim 1, wherein the RP is encased in a protein coat, a lipid vesicle, or any combination thereof.

4. The composition of claim 1, wherein the RP is encased in a viral vector.

5. The compositions of claim 4, wherein the viral vector is one of a double-stranded DNA virus, a single-stranded DNA virus, a single-stranded RNA virus, or a double-stranded RNA virus.

6. The compositions of claim 4, wherein the viral vector is an adeno-associated virus.

7. A composition that comprises a recombinant plasmid (RP) with a sequence of nucleotides that is SEQ ID NO. 3.

* * * * *

SEQUENCE LISTING

```
Sequence total quantity: 3
SEQ ID NO: 1          moltype = DNA  length = 5815
FEATURE               Location/Qualifiers
source                1..5815
                      mol_type = other DNA
                      organism = synthetic construct
SEQUENCE: 1
tctagaaagc ttcgataatc aacctctgga ttacaaaatt tgtgaaagat tgactggtat   60
tcttaactat gttgctcctt ttacgctatg tggatacgct gctttaatgc ctttgtatca   120
tgctattgct tcccgtatgg ctttcatttt ctcctccttg tataaatcct ggttgctgtc   180
tctttatgag gagttgtggc ccgttgtcag gcaacgtggc gtggtgtgca ctgtgtttgc   240
tgacgcaacc cccactggtt ggggcattgc caccacctgt cagctccttt ccgggacttt   300
cgctttcccc ctccctattg ccacggcgga actcatcgcc gcctgccttg cccgctgctg   360
gacaggggct cggctgttgg gcactgacaa ttccgtggtg ttgtcgggga aatcatcgtc   420
ctttccttgg ctgctcgcct gtgttgccac ctggattctg cgcgggacgt ccttctgcta   480
cgtcccttcg gccctcaatc cagcggacct tccttcccgc ggcctgctgc cggctctgcg   540
gcctctccg cgtcttcgcc ttcgccctca gacgagtcgg atctcccttt gggccgcctc   600
cccgcctaag cttatcgata ccgtcgagat ctaacttgtt tattgcagct tataatggtt   660
acaaataaag caatagcatc acaaatttca caaataaagc attttttttca ctgcattcta   720
gttgtggttt gtccaaactc atcaatgtat cttatcatgt ctggatctcg acctcgacta   780
gagcatggct acgtagataa gtagcatggc gggttaatca ttaactacaa ggaaccccta   840
gtgatggagt tggccactcc ctctctgcgc gctcgctcgc tcactgaggc cgggcgacca   900
aaggtcgccc gacgcccggg ctttgcccgg gcggcctcag tgagcgagcg agcgcgcagc   960
tggcgtaata gcgaagaggc ccgcaccgat cgcccttccc aacagttgcg cagcctgaat  1020
ggcgaatggc gattccgttg caatggctgg cggtaatatt gttctggata ttaccagcaa  1080
ggccgatagt ttgagttctt ctactcaggc aagtgatgtt attactaatc aaagaagtat  1140
tgcgacaacg gttaatttgc gtgatggaca gactcttta ctcggtgcc tcactgatta  1200
taaaaacact tctcaggatt ctggcgtacc gttcctgtct aaaatccctt taatcggcct  1260
cctgtttagc tcccgctctg attctaacga ggaaagcacg ttatacgtgc tcgtcaaagc  1320
aaccatagta cgcgccctgt agcggcgcat taagcgcggc gggtgtggtg gttacgcgca  1380
gcgtgaccgc tacacttgcc agcgccctag cgcccgctcc tttcgctttc ttcccttcct  1440
ttctcgccac gttcgccggc tttccccgtc aagctctaaa tcgggggctc cctttagggt  1500
tccgatttag tgctttacgg cacctcgacc ccaaaaaact tgattagggt gatggttcac  1560
gtagtgggcc atcgccctga tagacggttt ttcgcccttt gacgttggag tccacgttct  1620
ttaatagtgg actcttgttc caaactgaaa caacactcaa ccctatctcg gtctattctt  1680
ttgatttata agggattttg ccgatttcgg cctattggtt aaaaaatgag ctgatttaac  1740
aaaaatttaa cgcgaatttt aacaaaatat taacgtttac aatttaaata tttgcttata  1800
caatcttcct gtttttgggg cttttctgat tatcaaccgg ggtacatatg attgacatgc  1860
tagttttacg attaccgttc atcgattctc ttgtttgctc cagactctca ggcaatgacc  1920
tgatagcctt tgtagagacc tctcaaaaat agctaccctc tccggcatga atttatcagc  1980
tagaacggtt gaatatcata ttgatggtga tttgactgtc tccggccttt ctcaccgtt   2040
tgaatcttta cctacacatt actcaggcat tgcatttaaa atatatgagg gttctaaaaa  2100
tttttatcct tgcgttgaaa taaaggcttc tcccgcaaaa gtattacagg gtcataatgt  2160
ttttggtaca accgatttag ctttatgctc tgaggcttta ttgcttaatt ttgctaattc  2220
tttgccttgc ctgtatgatt tattggatgt tggaattcct gatgcggtat tttctcctta  2280
cgcatctgtg cggtatttca caccgcatat ggtgcactct cagtacaatc tgctctgatg  2340
ccgcatagtt aagccagccc cgacacccgc caacacccgc tgacgcgccc tgacgggctt  2400
gtctgctccc ggcatccgct tacagacaag ctgtgaccgt ctccgggagc tgcatgtgtc  2460
agaggttttc accgtcatca ccgaaacgcg cgagacgaaa gggcctcgtg atacgcctat  2520
ttttataggt taatgtcatg ataataatgg tttcttagac gtcaggtggc acttttcggg  2580
gaaatgtgcg cggaacccct atttgtttat ttttctaaat acattcaaat atgtatccgc  2640
tcatgagaca ataaccctga taaatgcttc aataatattg aaaaaggaag agtatgagta  2700
ttcaacattt ccgtgtcgcc cttattccct tttttgcggc attttgcctt cctgtttttg  2760
ctcacccaga aacgctggtg aaagtaaaag atgctgaaga tcagttgggt gcacgagtgg  2820
gttacatcga actggatctc aacagcggta agatccttga gagttttcgc cccgaagaac  2880
```

```
gttttccaat gatgagcact tttaaagttc tgctatgtgg cgcggtatta tcccgtattg  2940
acgccgggca agagcaactc ggtcgccgca tacactattc tcagaatgac ttggttgagt  3000
actcaccagt cacagaaaag catcttacgg atggcatgac agtaagagaa ttatgcagtg  3060
ctgccataac catgagtgat aacactgcgg ccaacttact tctgacaacg atcggaggac  3120
cgaaggagct aaccgctttt ttgcacaaca tgggggatca tgtaactcgc cttgatcgtt  3180
gggaaccgga gctgaatgaa gccataccaa acgacgagcg tgacaccacg atgcctgtag  3240
caatggcaac aacgttgcgc aaactattaa ctggcgaact acttactcta gcttcccggc  3300
aacaattaat agactggatg gaggcggata agttgcagg accacttctg cgctcggccc  3360
ttccggctgg ctggtttatt gctgataaat ctggagccgg tgagcgtggg tctcgcggta  3420
tcattgcagc actggggcca gatggtaagc cctcccgtat cgtagttatc tacacgacgg  3480
ggagtcaggc aactatggat gaacgaaata gacagatcgc tgagataggt gcctcactga  3540
ttaagcattg gtaactgtca gaccaagttt actcatatat actttagatt gatttaaaac  3600
ttcatttttta atttaaaagg atctaggtga agatcctttt tgataatctc atgaccaaaa  3660
tcccttaacg tgagttttcg ttccactgag cgtcagaccc cgtagaaaag atcaaaggat  3720
cttcttgaga tcctttttt ctgcgcgtaa tctgctgctt gcaaacaaaa aaaccaccgc  3780
taccagcggt ggtttgtttg ccggatcaag agctaccaac tctttttccg aaggtaactg  3840
gcttcagcag agcgcagata ccaaatactg tccttctagt gtagccgtag ttaggccacc  3900
acttcaagaa ctctgtagca ccgcctacat acctcgctct gctaatcctg ttaccagtgg  3960
ctgctgccag tggcgataag tcgtgtctta ccgggttgga ctcaagacga tagttaccgg  4020
ataaggcgca gcggtcgggc tgaacggggg gttcgtgcac acagcccagc ttggagcgaa  4080
cgacctacac cgaactgaga tacctacagc gtgagctatg agaaagcgcc acgcttcccg  4140
aagggagaaa ggcggacagg tatccggtaa gcggcaggt cggaacagga gagcgcacga  4200
gggagcttcc agggggaaac gcctggtatc tttatagtcc tgtcgggttt cgccacctct  4260
gacttgagcg tcgatttttg tgatgctcgt caggggggcg gagcctatgg aaaaacgcca  4320
gcaacgcggc cttttacgg ttcctggcct tttgctggcc ttttgctcac atgttctttc  4380
ctgcgttatc ccctgattct gtggataacc gtattaccgc cttgagtga gctgataccg  4440
ctcgccgcag ccgaacgacc gagcgcagcg agtcagtgag cgaggaagcg gaagagcgcc  4500
caatacgcaa accgcctctc cccgcgcgtt ggccgattca ttaatgcagc agctgcgcgc  4560
tcgctcgctc actgaggccg cccgggcaaa gcccgggcgt cgggcgacct ttggtcgccc  4620
ggcctcagtg agcgagcgag cgcgcagaga gggagtgcc aactccatca ctagggggtc  4680
cttgtagtta atgattaacc cgccatgcta cttatctacg tagccatgct ctaggacatt  4740
gattattgac tagtggagtt ccgcgttaca taacttacgg taaatggccc gcctggctga  4800
ccgcccaacg accccccgccc attgacgtca ataatgacgt atgttcccat agtaacgcca  4860
ataggggactt tccattgacg tcaatgggtg gagtatttac ggtaaactgc ccacttggca  4920
gtacatcaag tgtatcatat gccaagtacg cccctattg acgtcaatga cggtaaatgg  4980
cccgcctggc attatgccca gtacatgacc ttatggact ttcctacttg gcagtacatc  5040
tacgtattag tcatcgctat taccatggtc gaggtgagcc ccacgttctg cttcactctc  5100
cccatctccc cccccctccc acccccaatt ttgtattat ttattttta attattttgt  5160
gcagcgatgg gggcggggggg ggggggggc gcgcgccggg cggggcgagg  5220
ggcggggcgg ggcgaggcgg agaggtgcgg cggcagccaa tcagagcggc gcgctccgaa  5280
agtttccttt tatggcgagg cggcggcgg ggcggcccta taaaaagcga agcgcgcggc  5340
gggcgggagt cgctgcgcgc tgccttcgcc ccgtgccccg ctccgccgcc gcctcgcgcc  5400
gcccgccccg gctctgactg accgcgttac taaaacgagt aagtccggcc tccgcgccgg  5460
gttttggcgc ctcccgcggg cgcccccctc ctcacggcga gcgctgccac gtcagacgaa  5520
gggcgcagcg agcgtcctga tccttccgcc cggacgctca ggacagcggc ccgctgctca  5580
taagactcgg ccttagaacc ccagtatcag cagaaggaca ttttaggacg ggacttgggt  5640
gactctaggg cactggtttt cttttccagag agcggaacgg gcgaggaaaa gtagtccctt  5700
ctcggcgatt ctgcggaggg atctccgtgg ggcggtgaac gccgatgatg cctctactaa  5760
ccatgttcat gttttctttt tttttctaca ggtcctgggt gacgaacagg gtacc        5815

SEQ ID NO: 2            moltype = DNA   length = 2708
FEATURE                 Location/Qualifiers
source                  1..2708
                        mol_type = other DNA
                        organism = synthetic construct
SEQUENCE: 2
gccaccatgg ctactgggtc aagaacatct ctgctgctgg ctttcgggct gctgtgcctg  60
ccttggctgc aggaggggag tgctcaggtc cagctggtgg agtctggtcc tgcgctggtg  120
aaaccccacac agaccctcac actgacctgc agcttctctg ggttctcact caccactagg  180
agaatgtgtg tgagctggat ccgtcagacc ccagggaagg ccctggagtg gcttgcacgc  240
attgattggg atgatgataa agactacagc acatctctga agaccaggct caccatctcc  300
aaggacacct ccaaaaacca ggtggtcctt acaatgacca catgacccc tgtggacacg  360
gccacgtatt actgtgccac ggaccccacat ttatgatagt agtggttatt atctatacta  420
ctttgactac tgggggcagg gaaccctggt cacgtctgtc catccacaaa ggggtcacag  480
gtgtttcctc tggcccccatc tagcaagagc acatccggag gcaccgccgc cctgggatgt  540
ctggtgaagg attacttccc agagcccgtg accgtgtctt ggaacagcgg cgccctgaca  600
tccggagtgc acacctttcc agccgtgctg cagtcctctg gcctgtacag cctgagctcc  660
gtggtgcagtg tgccttctag ctccctgggc acacagagca tatctgcaa cgtgaatcac  720
aagcccagca ataccaaggt ggacaagaag gtggagccta gtcctgtga taagacacac  780
acctgcccac catgtcctgc accagagctg ctgggaggac atccgtgtt cctgtttcct  840
ccaaagccca aggacacact gatgatctct cgcacacccg aggtgacctg cgtggtggtg  900
gacgtgagcc acgaggatcc tgaggtgaag ttcaactggt acgtggatgg cgtggaggtg  960
cacaatgcca agacaaagcc tagagaggag cagtacaaca gcacatatcg ggtggtgtcc  1020
gtgctgacag tgctgcacca ggactggctg aacggcaagg agtataagtg caaggtgtcc  1080
aataaggccc tgcccgcccc tatcgagaag acaatctcta aggcaaaggg acagccaagg  1140
gagcctcagg tgtacaccct gccccttcc agggaggaga tgacaaagaa ccaggtgtct  1200
ctgacctgtc tggtgaaggg cttctatcct tccgacatcg ccgtggagtg ggagtctaat  1260
ggccagccag agaacaatta caagaccaca ccacccgtgc tggactccga tggctctttc  1320
tttctgtatt ctaagctgac cgtggataag agcagatggc agcagggcaa cgtgtttttct  1380
```

```
tgtagcgtga tgcacgaggc cctgcacaat cactacacac agaagtccct gtctctgagc   1440
ccaggcaaga ggaagaggag atccggatct ggagcaccag tgaagcagac cctgaacttc   1500
gacctgctga agctggccgg cgatgtggag agcaatccag gccccatggc cacaggcagc   1560
agaacctccc tgctgctggc cttttggcct ctgtgcctgc catggctgca ggagggaagc   1620
gccgatattg tgctgaccca gtctccatcc tccctgctgt catctatagg agacagagtc   1680
accatcactt gccgggcaag tcagaccatt gccagctatt taaatggtat cagcagaaac   1740
caggggaaagc ccctgaactc ctgatctatg ctgcaaccaa tttgcagagt ggggtcccat   1800
caaggttcag tggcagtgga tctgggacag atttcactct caccatcagc agtctgcgac   1860
ctgaagattt tgcaagttac tactgtcaac agagttacag tagtccctgg acgttcggcc   1920
aagggaccaa agtggatatc aaaaggacag cctaaggcag caccatccgt gaccctgttc   1980
ccaccttcct ctgaggagct gcaggccaat aaggccaccc tggtgtgcct gatcagcgac   2040
ttttaccctg gagcagtgac cgtggcatgg aaggccgata gctcccctgt gaaggccggc   2100
gtggagacaa caaccccatc taagcagagc aacaataagt acgcgcctc tagctatctg   2160
tctctgaccc cagagcaggg agaagccac cggtcttata gctgtcaggt gacccatgaa   2220
ggctcaactg tggagaaaac cgtcgcccca actgaatgtt cctaacgagc tcggtacctc   2280
tagatgctgg aggcttgctg aaggctgtat gctggccagg aactgaaatt gataccagtt   2340
ttggcctctg actgactggt atcaatcagt tcctggccag gacacaaggc ctgttactag   2400
cactcacatg gaacaaatgg cctctagcct ggaggcttgc tgaaggctgt atgctggcct   2460
gcgcgtgtga tgattaacag ttttggcctc tgactgactg ttaatcatca cgcgcaggcc   2520
aggacacaag gcctgttact agcactcaca tggaacaaat ggcctctagc ctggaggctt   2580
gctgaaggct gtatgctggc aaactgctga taccgaactg agttttggcc tctgactgac   2640
tcagttcggt cagcagtttg ccaggacaca aggcctgtta ctagcactca catggaacaa   2700
atggcctc                                                            2708

SEQ ID NO: 3          moltype = DNA  length = 8523
FEATURE               Location/Qualifiers
source                1..8523
                      mol_type = other DNA
                      organism = synthetic construct
SEQUENCE: 3
tctagaaagc ttcgataatc aacctctgga ttacaaaatt tgtgaaagat tgactggtat    60
tcttaactat gttgctcctt ttacgctatg tggatacgct gctttaatgc ctttgtatca   120
tgctattgct tcccgtatgg cttttcatttt tcctccttg tataaatcct ggttgctgtc   180
tctttatgag gagttgtggc ccgttgtcag gcaacgtggc gtggtgtgca ctgtgtttgc   240
tgacgcaacc cccactggtt ggggcattgc caccacctgt cagctccttt ccgggactt   300
cgctttcccc ctccctattg ccacggcgga actcatcgcc gctgccttg cccgctgctg   360
gacagggggc cggctgttgg gcactgacaa ttccgtggtg ttgtcgggga atcatcgtc   420
cttttccttg ctgctcgcct gtgttgccac ctggattctg cgcgggacgt ccttctgcta   480
cgtcccttcg gccctcaatc cagcggacct tccttcccg ggctgctgc cggctctgcg   540
gcctcttccg cgtcttcgcc ttcgccctca gacgagtcgg atctcccttt gggccgcctc   600
cccgcctaag cttatcgata ccgtcgagat ctaacttgtt tattgcagct tataatggtt   660
acaaataaag caatagcatc acaaatttca caaataaagc attttttttca ctgcattcta   720
gttgtggttt gtccaaactc atcaatgtat cttatcatgt ctggatctcg acctcgacta   780
gagcatggct acgtagataa gtagcatggc gggttaatca ttaactacaa ggaaccccta   840
gtgatggagt tggccactcc ctctctgcgc gctcgctcgc tcactgaggc cgggcgacca   900
aaggtcgccc gacgcccggg ctttgcccgg cggcctcag tgagcgagcg agcgcgcagc   960
tggcgtaata gcgaagaggc ccgcaccgat cgcccttcc aacagttgcg cagcctgaat  1020
ggcgaatggc gattccgttg caatggctgg cggtaatatt gttctggata ttaccagcaa  1080
ggccgatagt ttgagttctt ctactcaggc aagtgatgtt attactaatc aaagaagtat  1140
tgcgacaacg gttaatttgc gtgatggaca gactctttta ctcggtggcc tcactgatta  1200
taaaaacact tctcaggatt ctggcgtacc gttcctgtct aaaatccctt taatcggcct  1260
cctgtttagc tcccgctctg attctaacga ggaaagcacg ttatacgtgc tcgtcaaagc  1320
aaccatagta cgcgccctgt agcggcgcat taagcgcggc gggtgtggtg gttacgcgca  1380
gcgtgaccgc tacacttgcc agcgccctag cgcccgctcc tttcgctttc ttcccttcct  1440
ttctcgccac gttcgccggc tttccccgtc aagctctaaa tcgggggctc cctttagggt  1500
tccgatttag tgctttacgg cacctcgacc ccaaaaaact tgattagggt gatggttcac  1560
gtagtgggcc atcgccctga tagacggttt ttcgcccttt gacgttggag tccacgttct  1620
ttaatagtgg actcttgttc caaactggaa caacactcaa ccctatctcg gtctattctt  1680
ttgatttata agggattttg ccgatttcgg cctattggtt aaaaaatgag ctgatttaac  1740
aaaaatttaa cgcgaatttt aacaaaatat taacgtttac aatttaaata tttgcttata  1800
caatcttcct gtttttgggg cttttctgat tatcaaccgg ggtacatatg attgacatgc  1860
tagttttacg attaccgttc atcgattctc ttgtttgctc cagactctca ggcaatgacc  1920
tgatagcctt tgtagagacc tctcaaaaat agctaccctc tccggcatga atttatcagc  1980
tagaacggtt gaatatcata ttgatggtga tttgactgtc tccggcctttt ctcacccgtt  2040
tgaatcttta cctacacatt actcaggcat tgcatttaaa atatatgagg gttctaaaaa  2100
ttttatcct tgcgttgaaa taaggcttc tcccgcaaaa gtattacagg gtcataatgt  2160
ttttggtaca accgatttag ctttatgctc tgaggcttta ttgcttaatt tgctaattc  2220
tttgccttgc ctgtatgatt tattggatgt tggaattcct gatgcggtat tttctcctta  2280
cgcatctgtg cggtatttca caccgcatat ggtgcactct cagtacaatc tgctctgatg  2340
ccgcatagtt aagccagccc cgacaccgc caacacccgc tgacgcgccc tgacgggctt  2400
gtctgctccc ggcatccgct tacagacaag ctgtgaccgt ctccgggagc tgcatgtgtc  2460
agaggttttc accgtcatca ccgaaacgcg cgagacgaaa gggcctcgtg atacgcctat  2520
ttttataggt taatgtcatg ataataatgg tttcttagac gtcaggtggc acttttcggg  2580
gaaatgtgcg cggaacccct atttgtttat tttctaaat acattcaaat atgtatccgc  2640
tcatgagaca ataaccctga taaatgcttc aataatattg aaaaaggaag agtatgagta  2700
ttcaacattt ccgtgtcgcc cttattccct tttttgcggc attttgcctt cctgtttttg  2760
ctcacccaga aacgctggtg aaagtaaaag atgctgaaga tcagttgggt gcacgagtgg  2820
gttacatcga actggatctc aacagcggta agatccttga gagttttcgc cccgaagaac  2880
gttttccaat gatgagcact tttaaagttc tgctatgtgg cgcggtatta tccgtattg   2940
```

```
acgcgggca agagcaactc ggtcgccgca tacactattc tcagaatgac ttggttgagt    3000
actcaccagt cacagaaaag catcttacgg atggcatgac agtaagagaa ttatgcagtg    3060
ctgccataac catgagtgat aacactgcgg ccaacttact tctgacaacg atcggaggac    3120
cgaaggagct aaccgctttt ttgcacaaca tgggggatca tgtaactcgc cttgatcgtt    3180
gggaaccgga gctgaatgaa gccataccaa acgacgagcg tgacaccaca atgcctgtag    3240
caatggcaac aacgttgcgc aaactattaa ctggcgaact acttactcta gcttcccggc    3300
aacaattaat agactggatg gaggcggata aagttgcagg accacttctg cgctcggccc    3360
ttccggctgg ctggtttatt gctgataaat ctggagccgg tgagcgtggg tctcgcggta    3420
tcattgcagc actggggcca gatggtaagc cctcccgtat cgtagttatc tacacgacgg    3480
ggagtcaggc aactatggat gaacgaaata dacagatcgc tgagataggt gcctcactga    3540
ttaagcattg gtaactgtca gaccaagttt actcatatat actttagatt gatttaaaac    3600
ttcatttttta atttaaaagg atctaggtga agatcctttt tgataatctc atgaccaaaa    3660
tcccttaacg tgagttttcg ttccactgag cgtcagaccc cgtagaaaag atcaaaggat    3720
cttcttgaga tccttttttt ctgcgcgtaa tctgctgctt gcaaacaaaa aaaccaccgc    3780
taccagcggt ggtttgtttg ccggatcaag agctaccaac tctttttccg aaggtaactg    3840
gcttcagcag agcgcagata ccaaatactg tccttctagt gtagccgtag ttaggccacc    3900
acttcaagaa ctctgtagca ccgcctacat acctcgctct gctaatcctg ttaccagtgg    3960
ctgctgccag tggcgataag tcgtgtctta ccgggttgga ctcaagacga tagttaccgg    4020
ataaggcgca gcggtcgggc tgaacggggg gttcgtgcac acagcccagc ttggagcgaa    4080
cgacctacac cgaactgaga tacctacagc gtgagctatg agaaagcgcc acgcttcccg    4140
aagggagaaa ggcggacagg tatccggtaa gcggcagggt cggaacagga gagcgcacga    4200
gggagcttcc aggggggaaac gcctggtatc tttatagtcc tgtcgggttt cgccacctct    4260
gacttgagcg tcgatttttg tgatgctcgt caggggggcg gagcctatgg aaaaacgcca    4320
gcaacgcggc cttttttacgg ttcctggcct tttgctggcc ttttgctcac atgttctttc    4380
ctgcgttatc ccctgattct gtggataacc gtattaccgc ctttgagtga gctgataccg    4440
ctcgccgcag ccgaacgacc gagcgcagcg agtcagtgag cgaggaagcg gaagagcgcc    4500
caatacgcaa accgcctctc cccgcgcgtt ggccgattca ttaatgcagc agctgcgcgc    4560
tcgctcgctc actgaggccg cccgggcaaa gcccgggcgt cgggcgacct ttggtcgccc    4620
ggcctcagtg agcgagcgag cgcgcagaga gggagtggcc aactccatca ctaggggttc    4680
cttgtagtta atgattaacc cgccatgcta cttatctacg tagccatgct ctaggacatt    4740
gattattgac tagtgagtt ccgcgttaca taacttacgg taaatggccc gcctggctga    4800
ccgcccaacg accccgccc attgacgtca ataatgacgt atgttcccat agtaacgcca    4860
atagggactt tccattgacg tcaatgggtg gagtatttac ggtaaactgc ccacttggca    4920
gtacatcaag tgtatcatat gccaagtacg ccccctattg acgtcaatga cggtaaatgg    4980
cccgcctggc attatgccca gtacatgacc ttatgggact ttcctacttg gcagtacatc    5040
tacgtattag tcatcgctat taccatggtc gaggtgagcc ccacgttctg cttcactctc    5100
cccatctccc cccctcccc accccaatt ttgtatttat ttatttttta attatttgt    5160
gcagcgatgg gggcggggg ggggggggc gcgcgccagg cggggcgggg cggggcgagg    5220
ggcgggggcgg ggcgaggcgg ggcgaggcgg cggcagccaa tcagagcggc ggcgctccgga    5280
agtttccttt tatggcgagg cggcggcggc ggcggcccta taaaaagcga agcgcgcggc    5340
gggcgggagt cgctgcgcgc tgccttcgcc ccgtgccccg ctccgccgcc gcctcgcgcc    5400
gcccgccccg gctctgactg accgcgttac taaaacaggt aagtccggcc tccgcgccgg    5460
gttttggcgc ctcccgcggg cgccccctc ctcacggacg cgcctgccac gtcagacgaa    5520
gggcgcagcg agcgtcctga tccttccgcc cggacgctca ggacagcggc ccgctgctca    5580
taagactcgg ccttagaacc ccagtatcag cagaaggaca ttttaggacg ggacttgggt    5640
gactctaggg cactggtttt ctttccagag agcggaacag gcgaggaaaa gtagtcccttt    5700
ctcggcgatt ctgcggaggg atctccgtgg ggcggtgaac gccgatgatg cctctactaa    5760
ccatgttcat gttttctttt ttttctacaa ggtcctgggt gacgaacagg gtaccgccac    5820
catggctact gggtcaagaa catctctgct gctggctttc gggctgctgt gctgccttg    5880
gctgcaggag gggagtgctc aggtccagct ggtggagtct ggtcctgcgc tggtgaaacc    5940
cacacagacc ctcacactga cctgcagctt ctcggggtc tcactcacca ctaggagaat    6000
gtgtgtgagc tggatccgtc agcccccagg aaggccctg gagtggcttg cacgcattga    6060
ttgggatgat gataaagact acagcacatc tctgaagacc aggctcacca tctccaagga    6120
cacctccaaa aaccaggtgg tccttacaat gaccaacatg gaccctgtgg acacggccac    6180
gtattactgt gccacgacc cacatttatg atagtagtgg ttattatcta tactactttg    6240
actactgggg ccagggaacc ctggtcacgt ctcttcatcc acaaagggcc caagcgtgtt    6300
tcctctggcc ccatctagca agagcacatc cggaggcacc gccgcctgg gatgtctggt    6360
gaaggattac ttcccagagc ccgtgaccgt gtcttgaaac agcggcgccc tgacatccgg    6420
agtgcacacc tttccagccg tgctgcagtc tctggcctg tacagcctga gtccgtgact    6480
gacagtgcct tctagctccc tgggcacaca gacctatatc tgcaacgtga atcacaagcc    6540
cagcaatacc aaggtggaca agaaggtgga gcctaagtcc tgtgataaga cacacacctg    6600
cccaccatgt cctgcaccag agctgctggg aggaccatcc gtgttcctgt ttcctccaaa    6660
gcccaaggac acactgatga tctctcgcac acccgaggtg acctgcgtgg tggtggacgt    6720
gagccacgag gatcctgagg tgaagttcaa ctggtacgtg gatggcgtgg aggtgcacaa    6780
tgccaagacc aagccagag aggagcagta caacagcaca tatcgggtgg tgtccgtgct    6840
gaccgtgctg caccaggact ggctgaacgg caaggagtat aagtgcaagg tgtccaataa    6900
ggccctgccc gccctatcg agaagacaat ctctaaggca aagggacagc caagggagcc    6960
tcaggtgtac accctgcccc cttccaggga ggagatgaca aagaaccagg tgtctctgac    7020
ctgtctggtg aagggcttct atccttccga catcgccgtg gagtgggaga gtaatggcca    7080
gccagagaac aattacaaga ccacaccacc cgtgctggac tccgatggct ctttctttct    7140
gtattcaag ctgaccgtgg ataagagcag atggcagcag ggcaacgtgt ttcttgtag    7200
cgtgatgcac gaggccctgc acaatcacta cacacagaag tccctgtctc tgagcccagg    7260
caagaggaag aggagatccg gatctggagc caagtgaag cagaccctga acttcgacct    7320
gctgaagtgc tggagagcga tggagagcaa tgggcacag gggcagaac 7380
ctccctgctg ctggcctttg gcctgctgtg cctgccatgg ctgcaggagg aagcgccga    7440
tattgtgctg acccagtctc catcctccct gtctgcatct ataggagaca gagtcaccat    7500
cacttgccgg gcaagtcaga ccattgccag ctatttaaat ggtatcagca gaaaccaggg    7560
aaagcccctg aactcctgat ctatgctgca accaatttgc agagtggggt cccatcaagg    7620
ttcagtggca gtggatctgg gacagatttc actctcacca tcagcagtct gcgacctgaa    7680
```

-continued

```
gattttgcaa gttactactg tcaacagagt tacagtagtc cctggacgtt cggccaaggg  7740
accaaagtgg atatcaaaag gacagcctaa ggcagcacca tccgtgaccc tgttcccacc  7800
ttcctctgag gagctgcagg ccaataaggc caccctggtg tgcctgatca gcgactttta  7860
ccctggagca gtgaccgtgg catggaaggc cgatagctcc cctgtgaagg ccggcgtgga  7920
gacaacaacc ccatctaagc agagcaacaa taagtacgcc gcctctagct atctgtctct  7980
gaccccagag cagtggaaga gccaccggtc ttatagctgt caggtgaccc atgaaggctc  8040
aactgtggag aaaaccgtcg ccccaactga atgttcctaa cgagctcggt acctctagat  8100
gctggaggct tgctgaaggc tgtatgctgg ccaggaactg aaattgatac cagttttggc  8160
ctctgactga ctggtatcaa tcagttcctg gccaggacac aaggcctgtt actagcactc  8220
acatggaaca aatggcctct agcctggagg cttgctgaag gctgtatgct ggcctgcgcg  8280
tgtgatgatt aacagttttg gcctctgact gactgttaat catcacgcgc aggccaggac  8340
acaaggcctg ttactagcac tcacatggaa caaatggcct ctagcctgga ggcttgctga  8400
aggctgtatg ctggcaaact gctgataccg aactgagttt tggcctctga ctgactcagt  8460
tcggtcagca gtttgccagg acacaaggcc tgttactagc actcacatgg aacaaatggc  8520
ctc                                                                8523
```